United States Patent [19]

Cohen et al.

[11] Patent Number: 5,004,686

[45] Date of Patent: Apr. 2, 1991

[54] PROCESS FOR PRODUCING HUMAN EPIDERMAL GROWTH FACTOR AND ANALOGS THEREOF

[75] Inventors: Charles M. Cohen, Medway; Roberto Crea, Boston, both of Mass.

[73] Assignee: Creative Biomolecules, Inc., Hopkinton, Mass.

[21] Appl. No.: 140,739

[22] Filed: Jan. 4, 1988

Related U.S. Application Data

[62] Division of Ser. No. 832,337, Feb. 24, 1986, Pat. No. 4,743,679.

[30] Foreign Application Priority Data

Feb. 5, 1987 [AU] Australia .............................. 69011/87
Feb. 5, 1987 [CA] Canada ................................... 529101
Feb. 20, 1987 [EP] European Pat. Off. ........ 87301490.6
Feb. 27, 1987 [JP] Japan ................... 62-41229

[51] Int. Cl.$^5$ ........................ C12N 1/21; C12N 9/52; C12N 15/12; C12N 15/63; C12N 15/70; C12P 21/06

[52] U.S. Cl. .................................... 435/69.1; 435/69.7; 435/91; 435/701; 435/71.1; 435/170; 435/172.1; 435/172.3; 435/212; 435/252.3; 435/252.33; 435/320.1; 435/844; 536/27; 935/10; 935/22; 935/23; 935/24; 935/47; 935/48; 935/49; 935/51; 935/59; 935/60; 935/72; 935/73

[58] Field of Search ................ 435/69, 91, 170, 172.1, 435/172.3, 212, 252.3, 320, 70.1, 71.1, 849, 69.7, 252.33; 536/27; 935/10, 22, 23, 24, 47, 48, 49, 51, 59, 60, 61, 72, 73

[56] References Cited

U.S. PATENT DOCUMENTS

3,917,824 11/1975 Camble et al. ....................... 424/177
4,338,597 7/1982 Gilbert et al. .......................... 935/48

FOREIGN PATENT DOCUMENTS

046039 7/1981 European Pat. Off. ..
128733 6/1984 European Pat. Off. ..
131868 7/1984 European Pat. Off. ..
136490 8/1984 European Pat. Off. ..
0150572 10/1984 European Pat. Off. ..
0147178 12/1984 European Pat. Off. ..
0177915 10/1985 European Pat. Off. ..
2092155 12/1981 United Kingdom .
2162851A 2/1986 United Kingdom .
2172890A 10/1986 United Kingdom .
8304030 11/1983 World Int. Prop. O. .
8500369 1/1985 World Int. Prop. O. .
8501284 3/1985 World Int. Prop. O. .
8603779 2/1986 World Int. Prop. O. .
8602271 4/1986 World Int. Prop. O. .

OTHER PUBLICATIONS

Brake et al., 1984, *PNAS* 81: 4642–4646.
Hogg, 1981, *J. Biol. Chem.*, 256 (4): 1935–1939.

*Primary Examiner*—Robin L. Teskin
*Assistant Examiner*—Richard C. Peet
*Attorney, Agent, or Firm*—Lahive & Cockfield

[57] ABSTRACT

Disclosed is a process for producing a fusion protein of epidermal growth factor (EGF) attached through a Glu-residue, treatment of the fusion protein with a *Staphylococcus aureus* protease specific for cleaving peptides at a Glu-linkage thereby producing large amounts of the 53 amino acid EGF sequence.

The treatment conditions optimize production of large amounts of the 53 amino acid sequence relative to the 51 amino acid sequence minus the 52 Leu and 53 Arg residues and take full advantage of the selectivity of the protease.

9 Claims, No Drawings

PROCESS FOR PRODUCING HUMAN EPIDERMAL GROWTH FACTOR AND ANALOGS THEREOF

This is a division of application Ser. No. 832,337, filed Feb. 24, 1986, now U.S. Pat. No. 4,743,679.

TECHNICAL FIELD

The present invention relates to novel methods for preparing and using epidermal growth factor (EGF) and analogs thereof having biological activity.

BACKGROUND ART

Epidermal Growth Factor (EGF) and its analogs represent a family of polypeptides having a variety of biological activities. Human EGF itself is a 53 amino acid polypeptide and its analogs vary in the number of amino acids in the polypeptide chain. A variety of these have been described in the literature. For example, U.S. Pat. No. 3,917,824 issued Nov. 4, 1975 EGF. The literature has also described various biological activities for these materials. Each material may or may not have the same activity or as broad a biological activity as the others but in general, it has been found that EGF and analogs inhibit the secretion of gastric acid and promote cell growth. Thus they have been useful in wound healing applications.

Human EGF is found in the urine of young males, in the maxillary glands, and in various other locations throughout the body. Present production techniques of human EGF and its analogs stem largely from isolation of the active components from urine due to a lesser extent, from the recombinant DNA method for preparing these materials. The difficulty inherent in the first of these is quite apparent. Isolation from urine sources is time consuming, expensive and relies on the supply of raw material. Furthermore, the isolation of intact human EGF is made difficult by the presence of closely related analogs. Current procedures leading to a recombinant method for producing EGF have not been entirely satisfactory because of apparent instability of human EGF that results during its production and purification. Some of the disadvantages will become more apparent as more detail is described in this specification.

EGF, also known as urogastrone, is known to contain 53 amino acids as shown in the following sequence:

Formula 1

```
  1                  5                  10
  Asn Ser Asp Ser Glu Cys Pro Leu Ser His Asp 12                 17                 21
  Gly Tyr Cys Leu His Asp Gly Val Cys Met Tyr 23                 29                 32
  Ile Glu Ala Leu Asp Lys Tyr Ala Cys Asn Cys 34                 38                 43
  Val Val Gly Tyr Ile Gly Glu Arg Cys Gln Tyr 45                 49                 53
  Arg Asp Leu Lys Trp Trp Glu Leu Arg
```

The above formula is the formula for EGF as it exists in humans and as reported in the literature. The invention as described here, and for which more detail will be given later, relates to the microbial production of human EGF and some of its biologically active analogs. However, it is equally applicable to mouse EGF and in fact any EGF which has an equal or smaller number of glutamyl residues than human EGF.

It is to be noted in the sequence shown in formula I that residues 5, 24, 40 and 51 are glutamyl. The molecule in its natural form is folded in such a way that there are disulfide linkages between residues 6–20, 14–31, and 33–42.

While it is highly desirable to produce this material in recombinant DNA systems employing *E. coli*, there has been a significant obstacle to overcome because the *E. coli* tends to produce the EGF in its reduced form which is not stable to the bacterial endogenous proteases. It has been discovered and reported in the literature that in order to increase the stability, one should employ a leader sequence which results in an insoluble fusion protein and which therefore can be readily recovered from the cell paste. The selection of the specific leader sequence is known to be difficult and itself has created difficulty because at the end of the isolation phase of the polypeptide, the leader sequence must be separated and digested away from the EGF moiety at the N terminal amino group thereof. Similarly, even when an appropriate leader sequence is employed, great difficulty has been encountered in purifying the resulting polypeptide. It is often the case that chromatographic separations are required leading to a loss of product in an extremely tedious procedure.

DISCLOSURE OF THE INVENTION

The present invention provides recombinant DNA methods for producing novel EGF analogs as fusion proteins which include human EGF and analogs. It also relates to methods of introducing a glutamyl residue at the point of attachment of the leader sequence and the first amino acid of the EGF polypeptide. Finally, it provides biochemical methods for generating EGF and analogs from the fusion proteins through a specific preferential enzymatic cleavage of the Glu-residue preceding the amino acid sequence of EGF and analogs.

Various figures and tables are presented herein to show aspects of appropriate DNA sequences and amino acid sequences. For example, the amino acid sequence of a presently preferred embodiment of the EGF analogs of the present invention, together with the nucleic acid sequences of structural genes coding for the expression of these analogs and cleavage sites contained within said genes and;

the amino acid sequence of presently preferred embodiments of leader peptides constructed in accordance with the present invention, together with the nucleic acid sequence of DNA coding for the expression of this leader peptide and restriction endonucleus cleavage sites contained within said DNA sequence.

BEST MODE FOR PRACTICING THE INVENTION

In accordance with the present invention, novel EGF analogs are provided as fusion proteins containing EGF. Such fusion proteins can be cleaved in accordance with the present invention, selectively at the Glu cleavage site adjacent to the EGF by treatment with a Glu-specific protease.

It will be appreciated by those skilled in the art that a selective cleavage at the specific Glu-site is not obvious since there are four Glu-residues in the EGF molecule. In accordance with the present invention, however, it has been discovered that a Glu-specific protease can cleave the Glu at N-terminal end of the leader sequence without substantially altering the Glu-residues in the EGF molecule. It is thought that the specific folding of the molecule and the confirmational stability of the three disulfate linkages protect the internal Glu-residues from attack by the enzyme to a greater or lesser extent depending upon location in the molecule. Additionally the amino acid sequence that flanks the specific Glu-cleavage site can be designed to provide a preferential site for hydrolisis by a Glu-specific protease. Thus, for example, Glu-5, Glu-25 and Glu-40 are surprisingly not readily cleaved. However, Glu-51 can be readily cleaved because of its position at the C-terminal end of the hEGF. In practicing the preferred mode of the present invention, very low levels of the 1-25 and 1-40 analogs are produced, while about equal amounts of the 1-53 and 1-51 analogs are produced.

Also provided are DNA sequences capable of directing the expression of such analogs and fusion proteins whereby, in an appropriate expression vector, the structural gene for the EGF is in reading phase with a sequence of DNA coding for an additional sequence of amino acids together with a selective cleavage site so that expression of said DNA sequence provides a fusion protein comprising the EGF analog and a selective Glu-cleavage site adjacent to the analog.

Also provided in the present invention are microorganisms containing such expression vectors which, under appropriate times and conditions of incubation, can be induced to express the fusion proteins and analogs of the present invention.

The peptide compounds of the present invention generally comprise EGF analogs having the following formula:

X-Glu-EGF where X is a leader sequence oligopeptide of up to 200, preferably of up to 75 amino acids.

The EGF analog compounds will generally range from approximately 42 amino acids to polypeptides of about 53 amino acids and may be any of the active EGF fragments, the only requirement being that it be attached at its N-terminal amino acid residue to a Glu-residue at the C-terminus of the X-leader sequence.

Active analogs, having the common structural features previously disclosed can be produced in accordance with the disclosure of the present invention, allowing for variability in amino acid replacements in those areas where sequence conservation is low. Compounds within the scope of the present invention can be obtained by modifying the above recited formula in numerous ways while preserving the activity of the peptide compounds thus obtained.

For example, while amino acids of these peptides are normally in the L form, one or more, usually two or less and preferably one amino acid may be replaced with the optical isomer D form. Amino acid residues contained within the peptide compounds can also be modified by acylation or substituted with other chemical groups which can, for example, change the solubility of these compounds without affecting their biological activity.

In addition, one or more amino acid residues can be replaced by functionally equivalent residues; for example, basic polar amino acids can be replaced with other basic polar amino acids and acidic polar amino acids can be replaced with other polar amino acids. However, the replacement of certain amino acids, particularly cysteine, is considered less desirable due to the likelihood of interference with the formation of the cysteine disulfide bridges at 6-20, 14-31 and 33-42.

In general, X in the above formula are N-terminal extensions designated as leader peptides, which are designed to maximize the expression of the EGF and analogs in the chosen cellular expression system. These leader peptides have been designed to facilitate purification of the EGF fusion analog as provided in the examples. In accordance with the present invention a Glu-cleavage protease described below is used as the cleaving agent.

In accordance with the present invention, the leader peptides in the disclosed fusion protein have been designed to exclude any cysteine and any but an N-terminal methionine, and a C-terminal glutamic acid. The amino acid sequence of the presently preferred embodiment of a leader peptide in accordance with the present invention provides a cleavage site for *Staphylococcus aureous* V8 protease. Thus, the presently preferred embodiment provides a site for cleavage by a method which surprisingly does not interfere with the release of the active EGF and analogs.

Furthermore, the elimination of cysteine residues in the leader peptide prevents possible interactions and interferences with the obligatory formation of disulfide bridges in the active analogs.

In addition, the leader peptides should be of minimal length in order to avoid the synthesis of unnecessary amounts of leader peptide with the attendant inefficient use of the cellular machinery in transformed cell cultures.

One presently preferred embodiment of the leader peptides disclosed above is provided by the formula:

$X_1$ = Met Lys Ala Ile Phe Val Leu Lys Gly Ser     Formula 2

Leu Asp Arg Asp Leu Asp Ser Arg Leu Asp Leu Asp Val Arg

Thr Asp His Lys Asp Leu Ser Asp His Leu Val Leu Val Asp Leu

Ala Arg Asn Asp Leu Ala Arg Ile Val Thr Pro Gly Ser Arg Tyr

Val Ala Asp—

The presently preferred embodiment of the nucleic acid base sequence, which codes for the above X, is shown below in Formula 3. It will be readily appreciated that the DNA sequences and the structural gene used to provide for the expression of the fusion protein can be effectively replaced by equivalent nucleic acid sequences in accordance with the degeneracy of the genetic code. In addition, modifications in the amino acid sequence of the various leader peptides and analog compounds can be effected by changes in the nucleotide sequence of the cloned structural gene and DNA sequence used to direct synthesis of the analog and fusion protein. Included within such modifications of the DNA sequence are the replacement of various codons with other codons which direct the synthesis of the same amino acid. Also included are codon substitutions in which one or more amino acid residues can be replaced by functionally equivalent residues, as disclosed above.

Once the design of the DNA sequence is selected, it can be joined with other DNA sequences to enable replication and expression. Numerous vectors are available for expression such as e.g., microorganisms including bacteria and fungi, or various eukaryotic cells such as yeast or established cell lines. Hosts capable of harboring such vectors include *E. coli, S. crevisiae, B. subtilis,* mammalian cells and the like.

It is generally desirable to include at least one marker in the replication system to allow for the selection and maintenance of the DNA vector containing the synthetic DNA sequence in the host. Numerous markers are known in the art and include antibiotic resistance, heavy metal resistance and others.

The design of the fusion peptide which contains the EGF analog of interest will desirably facilitate the production of such analog in bacterial expression systems. In accordance with the present invention the leader peptide will be synthetic amino acid sequences designed to improve stability in the yield of the expression product and facilitate cleavage of the active EGF fragment by providing a Glu-residue at the point of attachment to the EGF. For example, a suitable fusion protein can form refractile bodies within the bacterial expression system and accumulate up to approximately 50% of the total protein content 25 of the bacterial cell.

However, insolubility of the fusion peptides contained in such refractile bodies can diminish the yield of the desired biologically active analog unless care is taken to ensure that fusion peptides will be susceptible to a solubility protocol.

Once the fusion protein has been obtained from the expression system, the leader peptide is desirably removed from the fusion protein to generate the biologically active EGF analog. While any cleavage may be employed, it is a feature of this invention that enzymatic cleavage can be performed at the Glu residue preceding the first amino acid of the biologically active EGF using the V8 *Staph. aureus* protease or any other selective Glu-cleaving enzyme.

Compounds of the present invention which are shown to have the above recited physiological effects can find use in therapeutical applications which benefit from improved cell growth characteristics. Thus these compounds can find use as therapeutic agents in wound healing applications such as burns, abrasions, treatment of gastric ulcer and the like.

These compounds can be administered to mammalian hosts for veterinary use such as with domestic animals, and clinical use in humans in a manner similar to other therapeutic agents both topically and systemically in a physiologically acceptable carrier. In general the dosage will range from about 0.001 to 100 mg/kg, of the host body weight. Dosages within these ranges can be used topically in an amount per administration which may vary depending on the severity of the condition treated until benefits have been obtained.

These compounds can be administered neat, as mixtures with other pharmacologically active or inactive materials, or with physiologically suitable carriers such as, for example, water or normal saline solution. The compounds can be administered parenterally, for example, by injection. Injection can be subcutaneous, intravenous, or by intramuscular injection.

These compounds are desirably administered in pharmaceutically effective amounts and often as pharmacologically acceptable salts such as acid addition salts. Such salts can include, e.g., hydrochloride, hydrobromide, phosphate, sulphate, acetate, benzoate, malate, among others.

Compounds of the present invention can also be used for preparing antisera for use in immunoassays employing labelled reagents, usually antibodies, conveniently, the compounds can be conjugated to an antigen by means of dialdehydes, particularly from 4 to 6 carbon atoms and aliphatic, or carbodiimide. These compounds and immunologic reagents may be labelled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The process of the present invention includes specific cleavage methods which facilitate production of maximum amounts of the 1-53 and 1-51 EGF analogs, with minimal amounts of the other analogs such as might be obtained by cleavage at the other glu-residues.

The examples will illustrate in detail preferred embodiments of the process conditions but in general they are as follows:

Following formation in the host system, the EGF fusion protein is precipitated in the cell and separated therefrom using standard techniques. In the preferred method, the fusion protein supernatants are obtained from urea solubilizations using preferably 8M urea, are placed on a chromatographic column and eluted therefrom with a suitable buffer/solvent mixture. The enriched EGF fusion protein is then treated with the Glu-cleaving protease, most preferably *Staphylococcus aureus* V8 protease (a suitable form is available from Miles Laboratories). The enzyme ratio is critical to achieving a maximum amount of 1-53 and 1-51 and minor amounts of other analogs. A suitable enzyme:substrate ratio ranges from 1:500 to 1:10,000 although 1:1,000 produces best results.

The time for hydrolysis usually runs from 8-15 hours, most preferably around 10-12 at elevated temperatures of from 32°-40° C., most preferably 37° C.

To explain more fully the details of the present invention, the following, together with illustrative examples, is presented.

RECOMBINANT DNA STANDARD METHODS

Practitioners in the art will be familiar with the general techniques of vector construction, transformation, DNA sequencing, probing techniques, site-directed mutagenesis and the like. Many of these techniques are described in standard laboratory manuals such as that of Maniatis, et al., *Molecular Cloning* (1982) Cold Spring Harbor Press.

However, for convenience, the conditions useful in the practice of the invention are suggested below. As will be seen from the examples set forth, modifications of and alternatives to these methods were sometimes used.

Vector Construction

DNA sequences derived from plasmids, phage, cDNA or synthetic fragments cloned into vectors may be manipulated using now standard techniques. In general, DNA sequences are cleaved using restriction enzymes (R.E.) which are commercially available. The conditions of cleavage as to pH, time, temperature, and concentration of enzyme are typically specified by the manufacturer. After each incubation, protein is removed by extraction, for example, with phenol/chloroform and the nucleic acid fraction is recovered by precipitation with ethanol. Size separation of the cleavage fragments may be performed using standard agarose or polyacrylamide gel electrophoresis techniques as described in Methods in Enzymology (1980) 65:499–560. Fragments may be blunted if desired by treating with *E. coli* DNA polymerase I (Klenow fragment) in the presence of the four deoxynucleotide triphosphates (dNTPs) using ambient temperature for about 30 minutes in 50 mM μM of the dNTPS. The extent of fill-in at the sticky ends may be, of course, regulated by appropriate choice of the dNTPs. Treatment under appropriate conditions with SI nuclease removes single stranded portions. Ligations are performed using T8-DNA ligase at pH 7.5 in Tris buffer, under condition recommended by the manufacturer.

Construction of correct DNA sequence is confirmed by transforming *E. coli* or other suitable host, selecting successful transformants using the appropriate antibiotic resistance or other markers, and isolating plasmids from transformations, for example, by the method of Clewell, et al., *Proc. Natl. Acad. Sci.* (19770 74:5463, as further described by Messing, et al., Nucleic Acids res (1981) 9:309 or by the method of Maxam, et al., Methods in Enzymology (1980) 65:499.

Transformation of DNA vectors into *E. coli* or other procaryotes is performed as described by Cohen, *Proc. Natl. Acad. Sci.* (1972) 69:110; for mammalian cells transformations are by the method of Graham and Van der Eb, *Virology* (1978) 52:546.

Alternatives and modifications of the foregoing methods are also employable, but the methods outlined above typify those useful in the invention.

Hosts and Control Sequences

The DNA fragments of the invention which encode for the EGF fusion analog can be used in a variety of expression systems to produce the desired proteins. Procaryotic systems most commonly utilize *E. coli* as host, although other bacterial strains such as Bacillus, Pseudomonas, or other Gram-positive or Gram-negative procaryotes can also be used. When procaryotic hosts are employed, control systems compatible with these hosts are ligated to the DNA fragments of the inventions into operable linkage and disposed on a suitable transfer vector which is capable of replication in the bacterial host cell. Backbone vectors capable of such replication include phage vectors and plasmid vectors, as is known in the art. Common plasmid vectors include those derived from pBR322 and the pUC series. Charon lambda phage is a frequent employed phage vector. Control sequences obligatorily include promoter and ribosome binding site encoding sequences and a variety of such controls are available in the art, most commonly the beta-lactamase (pencillinase) and lactose (lac) promoter systems, Chang et al., Nature (1977) 198:106, and the tryptophan (trp) promoter system, Goeddel, et al., Nucleic Acids Research (1980) 8:4057. Composite promoters containing elements of both the trp and lac promoter systems are also available in the art.

Eucaryotic microbes may also be used for expression, most commonly laboratory strains of *Saccharomyces cerevisiae*, or Baker's yeast. A number of yeast control systems and vectors are available, including those which are promoters for the synthesis of glycolytic enzymes, Hess, et al., J Adv Enzyme Reg (1968) 7:149; Holland, et al., Biochemistry (1978) 17:4900. Yeast vectors employing the 2 micron origin of replication are suitable as transfer vectors (see, for example, Broach, *Meth Enz* (1982) 101:307).

Tissue culture cells using cell lines immortalized from mammalian or other higher organisms have also been used as recombinant hosts. Such cell lines include chinese hamster ovary (CHO), vero, HeLa, and cos cells. In general, the Cos cell system is used for transient expression, while CHO cells typically integrate transformed DNA into the chromosome, suitable mammalian vectors are generally based on viral origins of replication and control sequences. Most commonly used are the simian virus 40 (SV40) promoters and replicons, Fiers, et al., Nature (1978) 273:113) and similar systems derived from Adenovirus 2, bovine papilloma virus, or avian sarcoma virus. The steps in constructing a microbial system and the biochemical methods used for producing EGF are described. The characteristic features of the described methods are applicable to the synthesis of other EGF analogs and EGF from other species and in particular to the synthesis of human EGF.

1. DNA Synthesis and Gene Ligation

In order to construct a DNA sequence capable of encoding the expression of the human EGF and analogs of interest, or a fusion protein containing said polypeptides, oligonucleotides are chemically synthesized, for example by solid phase phosphotriester methodology such as that described by Crea and Horn, Nucleic Acids Research, 8, 2331–2348 (1980) or by an automated system that uses the phosphite triester method such as described by Beaucage and Caruthers, *Tetrahedron Letters*, 22, 1859–1862 (1981).

Oligonucleotides used for gene synthesis vary in length, but generally range from 11 to 15 nucleotides. In order to construct double stranded DNA sequences, certain of the oligonucleotides comprise the upper strand and others comprise the lower strand of double stranded DNA. Certain portions of each oligonucleotide preferably overlap complementary regions of other oligonucleotides such that the complementarity with opposing fragments promotes self assembly through hydrogen bonding. Once assembled in this manner, the double stranded sequence can be completed by ligation using, for example, DNA Ligase.

Where the structural gene and DNA sequence coding for the expression of the desired human EGF or fusion protein is to be inserted in an expression vector, the gene or DNA sequence is preceded by a "start" codon, e.g., ATG, and immediately followed by one or more termination or stop codons. As described in further detail herein, the amino acid sequence of the fusion protein may be expressed which provides cleavage sites adjacent to the human EGF, preferably at or near the N-terminal end of the hEGF. Such cleavage sites will be coded by the appropriate codon(s) which define a leader peptide-EGF analog selective cleavage site.

In order to construct the structural gene for the presently preferred human EGF embodiment, the following 26 oligonucleotides were constructed, comprising the human EGF gene:

1: AATTCATGAACT
2: CTGACTCTGAATG
3: CCCGCTGAGCCAC
4: GACGGCTACTGCC

5: TGCACGACGGTGT
6: TTGCATGTACATC
7: GAAGCTCTGGACA
8: AATACGCATGCAA
9: CTGCGTTGTAGGC
10: TACATCGGCGAAC
11: GTTGCCAGTACCG
12: TGACCTGAAATGG
13: TGGGAACTGCGTTAG
14: GATCCTAACGCA
15: GTTCCCACCATTT
16: CAGGTCACGGTAC
17: TGGCAACGTTCGC
18: CGATGTAGCCTAC
19: AACGCAGTTGCAT
20: GCGTATTTGTCCA
21: GAGCTTCGATGTA
22: CATGCAAACACCG
23: TCGTGCAGGCAGT
24: AGCCGTCGTGGCT
25: CAGCGGGCAGGCA
26: GAGTCAGTTCATG

These sequences were constructed, in general, from dinucleotide reagents on a cellulose support using the phosphotriester method as described by Crea and Horn (1980).

In addition, the fusion peptide gene comprising the leader peptide genes $X_1$, $X_2$ and the Trp promoter gene (Formulae 3, 4, 5) and containing hEGF gene of the present invention are constructed by the synthesis and ligation of olignucleotide fragments. Except for the above oligonucleotides, the other DNA fragments used for the gene synthesis were synthesized from diisopropylphosphoramidite nucleotides (Beaucage and Caruthers, 1981) by using the automated stepwise addition protocol of Alvarado-Urbina et al., Science, 214, 270–274 (1981). A typical chemical synthesis using this latter method is described:

EXAMPLE 1

5'-(Dimethodxytrityl)-2'-deoxynucleosides (1 mmol) were converted into the corresponding diisopropylphosphoramidite derivatives in reaction mixtures containing 15 ml of anhydrous acetonitrile, 0.6 mL of dry 2,6-leutidine, and 0.2 ml of chloro (N,N-diisopropylamino) methoxyphosphine. After 15 minutes of shaking, 30 mL of 7 mg/mL 1H-tetrazole in acetonitrile was added to the reaction mixture. The resulting activated phosphoramidite derivatives were used for oligonucleotide synthesis on a derivatized silica support (Alvarado-Urbina et al., 1981). A typical addition cycle consisted of (a) addition of phosphoramidite derivative (1 min), (b) stop flow (1 min), (c) addition of 1% iodine in tetrahydrofuran-pyridine-water (3:1:1 v/v) (30 s), (d) pyridine wash (1.5 min), (e) methylene chloride wash (1 min), (f) wash with 3% trichloroacetic acid in methylene chloride (v/v) (1.5 min), (g) methylene chloride wash (1.5 min), and (h) acetonitrile wash (2 min). The flow rate was maintained at 5 mL/min for the entire cycle.

At the completion of synthesis, oligonucleotides were treated with dioxane-treithylamine-thiophenol (2:1:1 v/v) at room temperature for 45 min and then with concentrated ammonia at 55 C, overnight. The oligonucleotides were purified from the resulting mixture by thin-layer chromatography on Kieselgel 60 plates (Alvarado-Urbina et al., 1981). The purity and size of the final products were confirmed by electrophoretic analysis on polyacrylamide gels as described previously (Crea, et al., Proc. Natl. Acad. Sci., 75, 5765–5769, (1978)).

EXAMPLE 2

Gene Ligation

Oligonucleotides 2 to 13 and 15 to 26 were phosphorylated with Polynucleotide Kinase at 37 C for 1 h, in a reaction mixture containing oligonucleotides (1.2 ug of each) 1 mM ATP, t4-Polynucleotide kinase (1.3 units-/ug of DNA), 10 mM $MgCL_2$, 5 mM dithiothreitol and 70 mM Tris-HCL, pH 7.6.

Ligation of the oligonucleotides 1 to 26 was carried out at 15° C. for 2 hr in a reaction mixture containing 0.75 mM ATP, T4 DNA ligase (1.5 units/ug of DNA), 10 mM mgC12, 20 mM dithiothreitol, 50 ug/ml BSA, 50 mM Tris-HCl, pH 7.8. The DNA fragments were resolved by electrophoresis on 8% (w/v) polyacrylamide gels in the Tris-borate-EDTA buffer system described by Maniatis et al., Proc. Natl. Acad. Sci., 72, 1184–1188, (1975). Bands migrating at the expected molecular weight were sliced from the gel and were electroeluted (Maniatis et al., 1982). The eluted DNA was taken to dryness under vacuum and was resuspended in 200 L or 0.2M sodium acetate, pH 5. The sample was extracted twice with an equal volume of phenol, chloroform, and the DNA was precipitated with 2.5 volumes absolute ethanol. The purified gene fragments were stored in 4 C in 1 mM Tris-HCl and 0.1 mM EDTA, pH 7.5.

EXAMPLE 3

Amplification and Cloning of the Human EGF Gene

The synthetic hEGF gene was inserted into the EcoRI and BamHI sites of pUC8 (Viera and Messing, Gene. 19, 259–268, (1982). pUC8 96 µg) was digested at 37° C. in a 40 µL reaction mixture containing BamHI (32 units), 6 mM MgC12, 150 mM NaCl, 100 µg/mL BSA, and 6 mM Tris-HCL, pH 7.9. After 1 h, 6 µL of 1M Tris-HCl, pH 7.5, and 40 digestion was allowed to proceed at 37° C. for an additional 1 h. The DNA fragments were resolved by electrophoresis on a 6% (w/v) polyacrylamide gel. The large fragment was sliced from the gel and was electroeluted. The synthetic hEGF (30ng) and the large EcoRI/BamHI fragment of pUC8 (100 ng) were combined and treated with T4 DNA ligase. The ligation mixture was used to transform competent Escherichia coli K12 UT481 cells. Competent cells were prepared by using the low-pH methods described by Enea et al., J. Mol. Biol., 96, 495–509, (1975). Transformants were selected by plating on NZCYM agar (Maniatis et al., 1982) containing 25 µg/mL ampicillin. Plasmids were isolated from small cultures of transformed bacteria using a modification of the method of Birnboim and Doly, Nucleic A Res., 7, 1513–1523, (1979) as described by Maniatis et al. (1982). Purified plasmids were screened for the presence of the 170 base pair EGF gene insert by EcoRI and BamHI digestion, followed by polyacrylamide gel electrophoresis. Large scale preparations of plasmids containing the hEGF insert were done by using the alkaline lysis method of Birnboim & Doly (1979).

DNA Sequence Analysis

The DNA sequence of the cloned hEGF gene was determined by the dideoxynucleotide chain termination method (Sanger et al., Proc. Natl. Acad. Sci., 74, 5463–5467, 1977). pUC8 plasmid containing the hEGF gene was cleaved with EcoRI and BamHI, and the gene insert was purified by gel electrophoresis. The hEGF gene was inserted into the EcoRI and BamHI sites of M13 mp10w and mp11w (New England Biolabs, Messing, Methods Enzymol., 101, 20–78, 1983). Single-stranded M13 templates were prepared by using the method of Schreier and Cortese, J. Mol. Biol., 129, 169–172, (1979). DNA for the construction of a leader peptide and prometer.

The genes for the leader peptides $X_1$, $X_2$ and the synthetic Trp promoter (form Tables 3–5) were constructed from the enzymatic ligation of chemically synthesized fragments, cloned in plasmid pUC8, amplified and sequenced using similar procedure described for the above hEGF gene.

All the synthetic genes were assembled from oligonucleotides DNA Ligase under the same conditions reported for the synthesis of the EGF gene.

The gene corresponding to the leader X-1 was designed to bear a sticky end corresponding to the TaqI and BamHI restriction, endonuclease sites at the 5' and 3' ends respectively (see Formula 3). The gene corresponding to the Leader X-2 was designed with TaqI and BglII sticky ends (see Formula 4). Furthermore a synthetic gene corresponding to the Tryptophan (TRP) promoter was designed and assembled from oligonucleotides. This gene was designed with SacI and ClaI sticky ends (see Formula 5).

EXAMPLE 3

Cloning for the expression of fusion EGF analogs a. Construction of Glu-EGF gene.

The EGF synthetic gene (Formula 1) was modified at its N-terminal end to introduce a codon for the Glutamyl residue necessary for the specific enzymatic cleavage by *Staph. aureous* V8 protease.

In order to achieve this goal, the EGF gene cloned in pUC8 was retrieved as HinfI to HindIII fragment, where HinfII is a site present adjacent to the N-terminal end of the gene and HindIII is a site downstream from the BamHI site at the 3'- end of the synthetic gene.

A plasmid, pUC130XT, was designed to provide a very high number of restriction enzyme sites. The description of the plasmid and its assembly OXT is described below. This plasmid was digested with BglII and HindIII R.E. to provide the counterpart sticky sites. The EGF fragment and the plasmid were ligated together in a three piece ligation with the aid of a synthetic fragment, the sequence of which is as follows:

```
5' GAT CTG GAA AAC TCT G 3'
      AC CTT TTG AGA CTG A
   BglII                    Hinf I
```

This fragment will reconstitute the N-terminal of the EGF gene and place a codon for Glutamyl residue immediately before the first amino acid of the EGF. This new Glu-EGF gene was used for insertion in an expression vector constructed to generate fusion EGF analogs and described below.

b. Construction of a "universal" cloning vector pUC130XT

The plasmid pUC8 was used as the starting plasmid to construct a new cloning vector which has the advantage of having a higher number of R.E. sites and makes it a very flexible cloning vehicle. The pUC8 was digested with PvuII to eliminate the DNA fragment that comprises the polylinker DNA. This fragment was replaced with a correspondent PvuII fragment obtained from a commercially available double stranded M 13 vector (M13-TG130, Amersham) and containing an extended number of R.E. sites. Blue colonies were selected and the presence of the new multilinker DNA was confirmed by R.E. analysis. This plasmid was further modified by digesting the plasmid with EcoRI and KpnI and replacing this fragment with a synthetic fragment containing the R.E. sites for ClaI, NsaI, SphI and NcoI. This modification does not change the reading frame of the Lac region and therefore the new plasmid could be selected based on the blue phenotype so generated. This plasmid, widely used in our laboratory, has been called pUC130XT.

c. Cloning of the TRP promoter and leader peptides X-1 and X-2 in pUC130XT

The synthetic TRP Promoter was cloned into pUC130XT after plasmid digestion with SacI and ClaI. Subsequent to this experiment, the leader peptide X-2 gene was fused to the TRP promoter using the same procedures. (The bglII/bam hybrid site can be cleaved with XhoII or San3A). In order to transfer the constructs into an expression plasmid, the fragments containing the synthetic TRP adjacent to digestion with SmaI and PstI endonucleases. The SmaI site is present PstI is downstream from the carboxy-terminal of the two leader peptides.

d. Construction of an expression vector for the fusion EGF analogs

In order to construct an efficient expression vector, the plasmid pKK223-3, developed by Brosius et al. was selected. This plasmid carries a gene for Amp resistance where the original PstI site has been destroyed. This plasmid is tetracycline sensitive and produces only low quantity of DNA. We replaced the incomplete Tet gene with a complete and functional gene which was obtained from pBR322. The AvaI fragment, obtained from a pBR322 derivative containing a polylinker in the ecoRI site which places a SmaI (AvI) site adjacent to the EcoRI site, was used to substitute the corresponding AvaI fragment from pKK-223-3. We selected a plasmid which carries the Tet gene in an anti-clockwise orientation. This Tet resistant plasmid was digested with SmaI and PstI and ligated to the SmaI-PstI fragments obtained from pUC130XT, containing the RRP promoter next to the leader X-1 and X-2 respectively. Finally, the plasmid was digested with BglII and PstI and ligated to the Glu-EGF gene to generate complete plasmid containing the TRP promoter, and either of the leader peptides fused to the human EGF through the glutamyl residue. The two expression plasmids, pEGFXI and PEGFX2, so obtained bear the Tet gene and therefore can be used to transform competent *E. coli* cells and screen for Tet resistant tranformants.

e. Expression of Fusion polypeptide containing EGF

The expression plasmids, PEGFX1 and PEGFX2, were used to transform the *E. coli* strain JM83, under standard conditions. The transformed strain harboring the recombinant plasmids was selected and grown in M9 medium containing 20 mg/1 L-tryptophane (Miller, Experiments in Molecular Genetics, Cold Spring Harbour, 1972). These cells were used to inoculate 10 liter of the M9 medium in a 10 liter fermentor, enriched with additional glucose, 15 g/l and cas amino acids, 15 g/l, stirred at Ca. 400 rpm. All fermentations were at 37 C, pH 7.0 with an aeration rate of 1 v/v per minute.

Formula 3
Leader peptide X-1 gene:

```
              10           20          30
GCKCCATGAAAGCTATCTTCGTTTTAAAGGGTTCT
    Met Lys Ala Ile Phe Val Leu Lys Gly Ser
    AluI            MboII        DraI 40           50          60
CTCGATCGAGATCTGGACTCTCGTCTGGATCTG
 Leu Asp Arg Asp Leu Asp Ser Arg Leu Asp Leu
     PvuI    BglII       HinfI         Sau 3A
     Sau3A   Sau3A                     XhoI  I
     TagI TagI
          XhoII 70           80          90
GACGTTCGTACCGACCACAAAGACCTG
 Asp Val Arg Thr Asp His Lys Asp Leu
     MaeII   RsaI 100          110         120
TCTGATCACCTGGTTCTGGTCGACCTGGCT
 Ser Asp His Leu Val Leu Val Asp Leu Ala
     BclI     EcoRII        AccI EcoRII
     HphI                   HincII
     Sau3A ScrFI            SalI ScrFI
                            TaqI 130          140         150
CGTAACGACCTGGCTCGTATCGTTACTCCCGGGTCT
 Arg Asn Asp Leu Ala Arg Ile Val Thr Pro Gly Ser
     MaeIII    EcoRII       MaeIIIAvaI
               ScrFI        HpaII
                            NciI
                            NciI
                            ScrFI
                            ScrFI
                            SmaI
                            XmaI 160          170         180
CGTTACGTTGCGGATCC
 Arg Tyr Val Ala Asp
     MaeII       BamH1
     MeaIII      BamH1
                 Sau3A
                 XhoII
```

| restriction sites in the leader peptide X-1 | | | | |
|---|---|---|---|---|
| imprleab.seq | 173 nucleotides. | | | |
| AccI | 109 | | | |
| AluI | 6 | | | |
| AvaI | 148 | | | |
| BamH1 | 168 | | | |
| BclI | 93 | | | |
| BglII | 39 | | | |
| DraI | 18 | | | |
| EcoRII | 99 | 114 | 129 | |
| HincII | 109 | | | |
| HinfI | 46 | | | |
| HpaII | 149 | | | |
| HphI | 96 | | | |
| MboII | 11 | | | |
| NciI | 148 | 149 | | |
| NlaIV | 168 | | | |
| PvuI | 33 | | | |
| RsaI | 71 | | | |
| SalI | 109 | | | |
| Sau3A | 34 | 40 | 58 | 94 | 169 |
| ScrFI | 99 | 114 | 129 | 148 | 149 |
| SmaI | 148 | | | |
| TagI | 32 | 36 | 110 | |
| XhoII | 39 | 57 | 168 | |
| XmaI | 148 | | | |
| MaeII | 65 | 161 | | |
| MaeIII | 122 | 142 | 158 | |

Formula 4
Leader peptide X-2 gene.

16 NUCLEOTIDES.
MW for gene product 1 = 2546. Number of amino acids = 24

| AluI | 29 | 50 | |
|---|---|---|---|
| BbvI | 27 | 48 | |
| BglII | 71 | | |
| DdeI | 10 | 31 | 52 |
| Fnu4HI | 27 | 48 | |
| NcoI | 4 | | |
| NlaIII | 5 | | |
| Sau3A | 72 | | |
| SfaNI | 24 | 45 | 66 |
| StyI | 4 | | |
| XhoI | 71 | | |

```
              10           20          30
*CGACCATGGCTAAGAACCTGAACGATGCAGCTAAG
     Met Ala Lys Asn Leu Asn Asp Ala Ala Lys
     NcoI    DdeI             SfaNI AluI
     NlaIII                   BbvI DdeI
     StyI                     Fnu4HI 40           50          60
AACCTGAACGATGCAGCTAAGAACCTGAAC
 Asn Leu Asn Asp Ala Ala Lys Asn LEU Asn
                 SfaNI AluI
                 BbvI DdeI
                 Fnu4HI

70
                            GATGCAGATCT
                            Asp Ala  Asp
                            SfaNI BglII
                                 Sau3A
                                 XhoII
```

*CG is sticky end of taqI site. This site was used to join the helix with the taqI (claI site) of the synthetic trp promoter.

Formula 5
SYNTHETIC TRP PROMOTER

| snpropat. seq | | 93 nucleotides. | |
|---|---|---|---|
| AluI | 2 | | 24 |
| BanII | 1 | | |
| Bspl286 | 1 | | |
| ClaI | 84 | | |
| HgiAI | 1 | | |
| HincII | 28 | | 51 |
| HpaI | 51 | | |
| NlaIII | 90 | | |
| RsaI | 59 | | |
| SacI | 1 | | |
| Sau3A | 87 | | |
| SpeI | 47 | | 55 |
| SspI | 10 | | |
| TaqI | 43 | | 85 |
| MaeI | 48 | | 56 |
| MaeII | 71 | | |

```
              10           20          30
GAGCTCGCAAATATTCTGAAATGAGCTGTTGACA
TCGAGCGTTTATAAGACTTTACTC GACAACTGT
    AluI        SspI              AluI HincII
    BanII
    HgiAI
    SacI 40           50          60
ATTAATCATCGAACTAGTTAACTAGTADGCAA
TAATTAGTAGCTTGATCAATTGATCATGCGTT
    TagI SpeI HinckII              RsaI
         HpaI SpeI
         MaeI     MaeI
```

-continued

```
         70            80           90
    GTTCACGTAAAAAGGGTATCGATCATG
    CAAGTGCATTTT TCC CATAGC
         MaeII           ClaI  NlaIII
                               Sau3A
                               TaqI
```

EXAMPLE 4

Isolation and Purification of the Fusion Protein

The EGF fusion protein is precipitated in the host cell following its synthesis. These light refractile bodies are differentially solubilized from other cell material and provide the basis for an 80% product enrichment. All procedures are carried out at 4° C. The cell paste is suspended in 25 mM Tris, 10 mM EDTA, pH 8.0 (10 ml/g cell paste), treated with lysozyme (1 mg/g cell paste) (Sigma Chemical Co.) and allowed to stir 30 minutes. The suspension is sonicated 3 times (3 minutes) with 5-minute cooling periods between sonications (Fisher Sonic Dismembrator, Model 300, setting 60%). The resulting suspension is centrifuged at 17,000 rpm for 20 minutes (Bechman Instruments, Model J2-21M, JA-17 Rotor). The pellet is resuspended in the same buffer and homogenized (Dupont Omnimixer Model 17105) for 30 seconds at #4 setting. The resulting homogenate is centrifuged as above, except this and all subsequent centrifugations are for 15 minutes. The pellet is resuspended in a 95% volume of the same buffer, and homogenized as above. After mixing, sufficient concentrated Triton X-100 is added to result in a suspension with a final detergent concentration of 1%. The suspension is allowed to stir for 30 minutes and is centrifuged as above. The resulting pellet is resuspended in diluted buffer(2.5 mM Tris, 1.0 mM EDTA, pH 8.0), homogenized and centrifuged as above. The pellet is resuspended in the diluted buffer containing 8M Urea (5 ml buffer/g cell paste), homogenized and centrifuged as above. All supernatants are evaluated for the presence of the fusion protein using 15% SDS polyacrylamide gel electrophoresis. Following centrifugation, the product enriched supernatant is applied to a DEAE-52 chromatographic column (Whatman Chemicals). The size of the column is determined by amount of sample to be processed. The column is slurry packed and equilibrated with 2.5 mM Tris, 1.0 mM EDTA, 6 Murea, pH 8.0. The protein is eluted with a continuous salt gradient (0–250 mM NaCl). Column fractions are monitored spectrophotometrically at 280 nm and fraction aliquots are run on 15% SDS PAGE. EGF fusion containing fractions are then pooled and dialyzed against several changes of the buffer used for the proteolysis step (100 mM Ammonium acetate, 1 mM EDTA, pH 7.8). The protein concentration of the dialysate is determined by UV scan. The EGF fusion protein is approximately 95% pure as determined by HPLC using a reverse phase C18 column (4.6 mm×250 mm, Vydac). The protein is eluted with a continuous gradient (buffer A is 0.05% TFA/$H_{20}$; buffer B is 0.035% TFA/Acetonitrile, pH 2). The enriched EGF fusion protein is then treated with *Staphylococcus aureus* V8 protease (Miles Laboratories) at an enzyme:substrate ratio of 1:1000 for 12 hours at 37° C. The products following digestion are purified using reverse phase C18 chromatography with a continuous gradient (buffer A is 10 mM sodium phosphate, pH 6.2; buffer B is acetonitrile). Approximately equal quantities of the 1–53 and 1–51 analogs are obtained.

Amino Acid Analysis

All chemicals and solvents are HPLC grade (J. T. Baker Chemical Co./VWR Scientific). Samples for amino acid composition analysis were hydrolyzed in vacuo in 0.2 ml 6N constant-boiling HCL (Pierce Chemical Co.) for 24 hours at 110° C. Following hydrolysis, samples were dried in a vacuum desiccator over sodium hydroxide pellets and dissolved in HPLC grade water to an approximate concentration of 100 pm/20 μl. The fully automated procedure is an adaptation of a method for pre-column derivatization with OPA (o-phthalaldehyde) described by H. Jones, et al. (J. Liquid Chromatog. 4(4), 565–596, 1981). OPA (Fluoropa, Pierce Chemical Co.) is prepared as follows: 100 mg OPA is dissolved in 2.0 ml methanol, then 19.0 ml 0.4M Sodium borate pH 9.5 (prepared from sodium tetraborate) and 100 μl 2-mercaphoethanol (Bio-Rad Laboratories) is added. Working solution, prepared fresh daily, is prepared by diluting 750 μl above OPA stock with 3.25 ml borate buffer. Amino acids standards, also prepared fresh daily, are diluted to a concentration of 100 pm/20 μl injection with HPLC grade water.

Sequencing and PTH Analysis

Amino acid sequence determinations were carried out by automated Edman degradation with a gas-phase sequencer Applied Biosystems, Model 470A, using standard techniques. EGF was digested with Trypsin at an enzyme to substrate ratio of 1:10 (w/w) and the resulting peptides were separated by HPLC and identified to confirm production of EGF using 1–53 and 1–51 automated sequence analysis:

Asn—Ser—Asp—Ser—Glu—Cys—Pro—Leu—Ser—His—asp—Gly—  12

Tyr—cys—Leu—His—Asp  Gly—Val—Cys—Met—Tyr—Ile—Glu—  24

Ala—Leu—Asp—Lys—Tyr—Ala—Cys—Asn—Cys—Val—Val—Gly—  36

Tyr—Ile—Gly—Glu—Arg—Cys—Gln—Tyr—Arg—Asp—Leu—Lys—  48

Trp—Trp—Glu—Leu—Arg  53

All residues underlined have been identified by direct sequence analysis. Cys is determined by standard chemical procedures following sequence analysis.

Receptor binding Assay for Epidermal Growth Factor (EGF)

The biological activity of the 1–53 and 1–51 EGF were quantitated using a competitive radiometric assay measuring binding to receptors on epidermal cells.

What is claimed is:

1. A method for producing an epidermal growth factor or a biologically active analog of an epidermal growth factor comprising the steps of:

A. constructing a vector including a DNA sequence encoding a fused polypeptide having the formula:

X—Glu—EGF wherein X is a leader sequence oligopeptide which serves to promote expression of said fused polypeptide in said host cell, Glu is a linking glutamyl residue, and EGF is the amino acid sequence of an epidermal growth factor or an active analog thereof, said EGF being attached at its N-terminal end to said linking Glu residue, and said linking Glu residue being attached to the C-terminal end of said leader sequence oligopeptide;

B. transfecting a microbial host cell with said vector;
   C. expressing said DNA sequence in said host cell to produce a fused polypeptide;
   D. isolating said fused polypeptide from said host cell; and
   E. treating said fused polypeptide with *Staphylococcus aureus* V8 protease under conditions and for a time suitable to preferentially cleave said fused polypeptide at said linking glutamyl residue to release said EGF.

2. The method of claim 1 comprising the additional step of dissolving said fused polypeptide in urea and concentrating the resulting solution prior to step E.

3. The method of claim 1 wherein, during step E, the molar ratio of *Staphylococcus aureus* V8 protease to said fused polypeptide is within the range of 1:500 to 1:10,000.

4. The method of claim 1 wherein step E is conducted for between 8 and 12 hours.

5. The method of claim 1 wherein step E is conducted at a temperature between 32° C. and 40° C.

6. The method of claim 1 wherein said EGF comprises an EGF analog comprising between 42 and 53 amino acids.

7. The method of claim 1 wherein said EGF comprises 51 amino acids.

8. The method of claim 1 wherein said X has the amino acid sequence:

Met Ala Lys Asn Leu Asn Asp Ala Ala Lys Asn Leu

Asn Asp Ala Ala Lys Asn Leu Asn Asp Ala Asp .

9. The method of claim 1 wherein said microbial host cell is an *E. coli* strain.